US00PP17840P3

(12) United States Plant Patent
Danziger

(10) Patent No.: US PP17,840 P3
(45) Date of Patent: Jul. 3, 2007

(54) ***SCAEVOLA* PLANT NAMED 'SCABLHATIS'**

(50) Latin Name: *Scaevola aemula*
Varietal Denomination: Scablhatis

(75) Inventor: Gabriel Danziger, Moshav Nir Zvi (IL)

(73) Assignee: Syngenta Seeds B.V., Enkhuizen (NL)

( * ) Notice: Subject to any disclaimer, the term of this patent is extended or adjusted under 35 U.S.C. 154(b) by 346 days.

(21) Appl. No.: 11/030,024

(22) Filed: Jan. 6, 2005

(65) Prior Publication Data

US 2006/0150290 P1 Jul. 6, 2006

(51) Int. Cl.
*A01H 5/00* (2006.01)

(52) U.S. Cl. ..... Plt./363

(58) Field of Classification Search ..... Plt./363
See application file for complete search history.

*Primary Examiner*—Kent Bell
*Assistant Examiner*—June Hwu
(74) *Attorney, Agent, or Firm*—Bruce Vrana

(57) ABSTRACT

A new and distinct *Scaevola* plant named 'Scablhatis', characterized by its spreading and cascading growth habit and blue flowers that have a big light yellow eye.

1 Drawing Sheet

Latin name of the genus and species of the plant claimed: *Scaevola aemula.*
Varietal denomination: 'Scablhatis'.

BACKGROUND OF THE NEW PLANT

The present invention comprises a new and distinct cultivar of *Scaevola* plant, botanically known as *Scaevola aemula,* synonym *Scaevola saligna* and hereinafter referred to by the cultivar name 'Scablhatis.'

The new cultivar originated from a cross made in 1999 of two selections of *Scaevola aemula:* 'SC100' as female parent and an open pollinated unidentified variety as pollen male parent. Both of these selections are not commercially available and not known by any synonyms.

The new *Scaevola* plant was selected as a flowering plant within the progeny of this cross in a controlled environment in Enkhuizen, The Netherlands. Plants of the new *Scaevola* have blue flowers whereas plants of the unidentified selections have purple/blue flowers which is typical for the species *Scaevola aemula.*

The new *Scaevola* plant has been asexually reproduced by cuttings in Enkhuizen, The Netherlands and Sarrians, France over a two year period. It has been found to retain its distinctive characteristics through successive propagations, and this novelty appears to be firmly fixed.

SUMMARY OF THE INVENTION

The new cultivar has not been observed under all possible environment conditions. The phenotype may vary somewhat with variations in environmental such as temperature, day length and light intensity, without, however, any variance in genotype. This description is made under the following greenhouse conditions: day length: from 13 to 15 hours per day, temperature: day 22 degrees Celsius, night 16 degrees Celsius.

The following characteristics have been repeatedly observed and are determined to be basic characteristics of 'Scablhatis,' which distinguish 'Scablhatis' as a new and distinct cultivar.

1) Low-growing, spreading and cascading growth habit.
2) Medium internodes, dense and bushy plant form and freely branching plant habit.
3) Very freely flowering, more than 600 flowers and flower buds per plant.
4) Unique very large blue fan-shaped flowers with light green-yellow eye.

DESCRIPTION OF THE DRAWING

This new *Scaevola* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Scaevola* plant. The data that define these characteristics were collected from asexual reproductions carried out in Enkhuizen, Netherlands. The plant history was taken on 16 week old plants, blossomed under natural light in a greenhouse and grown in a 13 cm container. Colour readings were taken in the greenhouse under ambient light. Colour references are primarily to The R.H.S. Colour Chart of The Royal Horticultural Society of London.

TABLE 1

Differences between the new cultivar 'Scablhatis', its parents and a similar cultivar

| | 'Scablhatis' | 'SC100' | 'MALE' | 'Newon' |
|---|---|---|---|---|
| Flower color | Blue with eye | Blue with eye | Open pollination | Blue with eye |
| Flower size | | | | |
| Length | 2.6–3.2 cm | 2.5–3 cm | Open pollination | 3.0–3.6 cm |

TABLE 1-continued

| Differences between the new cultivar 'Scablhatis', its parents and a similar cultivar | | | | |
|---|---|---|---|---|
| | 'Scablhatis' | 'SC100' | 'MALE' | 'Newon' |
| Width | 2.8–3.4 cm | 2.8–3.2 cm | Open pollination | 3.2–3.8 cm |
| Size of eye zone | 0.2 cm | | Open pollination | 0.4 cm |
| Shoot length | 40–60 cm | | Open pollination | 60–90 cm |
| Seed set | Abundant | | Open pollination | None |

The most resembling variety 'Newon' is patented as U.S. Plant Pat. No. 10,584.

Botanical classification: *Scaevola aemula.*

Parentage:

*Female parent.*—A seedling named 'SC100' is one of our seedlings from our A-generation of plants bred in 1998.

*Male parent.*—A seedling named 'MALE' is one of our seedlings from our A-generation of plants bred in 1998.

Propagation:

*Type cutting.*—Terminal cuttings.

*Time to initiate roots* (*summer*).—About 10–16 days at 24 degrees C.

*Time to develop roots* (*summer*).—About 20 days at 24 degrees C.

*Root description.*—Numerous, fine, freely branching.

The plant:

*Plant form and growth habit.*—Semi-erect, later spreading.

*Plant height.*—About 28 cm.

*Plant width* (*spread*).—About 68 cm.

*Branching character.*—Freely branching and lateral branching at every node.

*Quantity of branches.*—40–50 per plant.

*Blooming period.*—From May until November.

The stem:

*Diameter.*—2–4 mm.

*Shape.*—Round.

*Color.*—141B.

*Anthocyanin pigmentation.*—Present, color 176A.

*Length of internode.*—3.8–5.2 cm.

*Texture.*—Smooth, no pubescence.

The foliage:

*Phyllotaxis.*—Alternate, single.

*Shape of blade.*—Lanceolate to oblanceolate.

*Texture.*—Upper side: Smooth. Lower side: Smooth.

*Anthocyanin pigmentation.*—Present, color 179C.

*Attachment to leaf.*—Petiolate.

*Venation.*—Pinnate.

*Leaf margin.*—Dentate.

*Leaf base.*—Attenuate.

*Leaf apex.*—Acute.

*Length.*—Gradual size reduction towards lateral branch apex until leaves subtending flowers apprear bract-like.

*Length.*—Lower leaves: 4.1–4.8 cm. Higher leaves: 1.1–1.4 cm.

*Width.*—Lower leaves: 1.9–2.8 cm. Higher leaves: 0.3–0.4 cm.

*Depth of incision.*—0.2–0.3 cm.

*Color.*—Upper side: 137A. Lower side: 137C.

*Petiole.*—Length: 0.5 cm. Width: 0.3 cm. Color: 137A.

The bud:

*Size of the bud.*—Length: 1.8–2.2 cm. Diameter: 0.2 cm.

*Shape.*—Elliptic. Apex: Acute. Base: Cuneate.

*Anthocyanin pigmentation.*—Present, color 179C.

*Color.*—N144C.

*Sepals.*—Color Base: N144C. Apex: 143A. Form: Opposite. Number: 2, parted. Size Length: 0.7 cm. Width: 0.15 cm. Shape: Ligulate. Margin: Entire. Texture: Smooth.

The flower:

*Form.*—Zygomorphic, semi-circular, fan-shaped with five petals fused at the base to form a tubular flower throat. Flower throat open along the upper surface exposing reproductive organs.

*Flower width.*—2.8–3.4 cm.

*Flower length.*—2.6–3.2 cm.

*Flower aspect.*—Horizontal to stem.

*Flower arrangement.*—Solitary, one flower per leaf axil, flowers sessile.

*Color.*—Upper side: Between 92A and 92B. Lower side: 92C. Middle stripe upper side: 92A. Middle stripe lower side: 155D.

*Color of the eye.*—150C.

*Size of the eye.*—0.2 cm.

*Perianth.*—Aspect: Fan-shaped, flat. Length, fan: About 2.9 cm. Width, fan: About 3.2 cm. Height: About 1.8 cm.

*Inner tube color.*—6D.

*Outer tube color.*—92C.

*Overlapping of the petals.*—Almost separate, fused at the base.

*Number of petals.*—Five.

*Shape of the petals.*—Oblanceolate.

*Apex.*—Mucronate.

*Margin.*—Entire.

*Surface texture.*—Smooth.

*Size.*—Width: 0.5 cm. Length: 1.5 cm.

*Number of flowers per lateral branch.*—80–100.

*Number of flowers at one time open.*—6–12.

*Fragrance.*—No fragrance.

*Lastingness of the individual flower.*—3–4 days.

*Lastingness of the bloom.*—New flowers continue to open in one inflorescence for 30 days.

The reproductive organs:

*Androecium.*—Stamen number: Five. Anther shape: Oblong. Anther length: 1–2 mm. Anther diameter: Less than 1 mm. Anther color: 165B. Amount of pollen: Normal. Pollen color: 165B.

*Gynoecium.*—Pistil number: 1. Pistil length: 1–1.6 cm. Style length: 1 cm. Style color: 144C. Stigma color: 144C. Stigma shape: Oblong. Ovary color: 144C.

The seed: From one flower on seed is formed; with one embryo within. Seed set is abundant in later season. From every flower, one seed is produced. The seed is hard coated, so little germination occurs without scarification.

*Size.*—Length: 1.5–2 mm. Width: 1 mm.

*Texture of the surface.*—Smooth.

*Color when fallen from plant.*—146D.

*Color when ripe.*—166B.

Disease/pest resistance: No resistance to pests and diseases common to *Scaevola* (mainly Verticillium and Phtophtora) is observed.

Temperature tolerance: Plants of the new *Scaevola* have been observed to tolerate temperatures from 2 to 30 degrees C.

What is claimed is:

1. A new and distinct *Scaevola* plant named 'Scablhatis', substantially as illustrated and described herein.

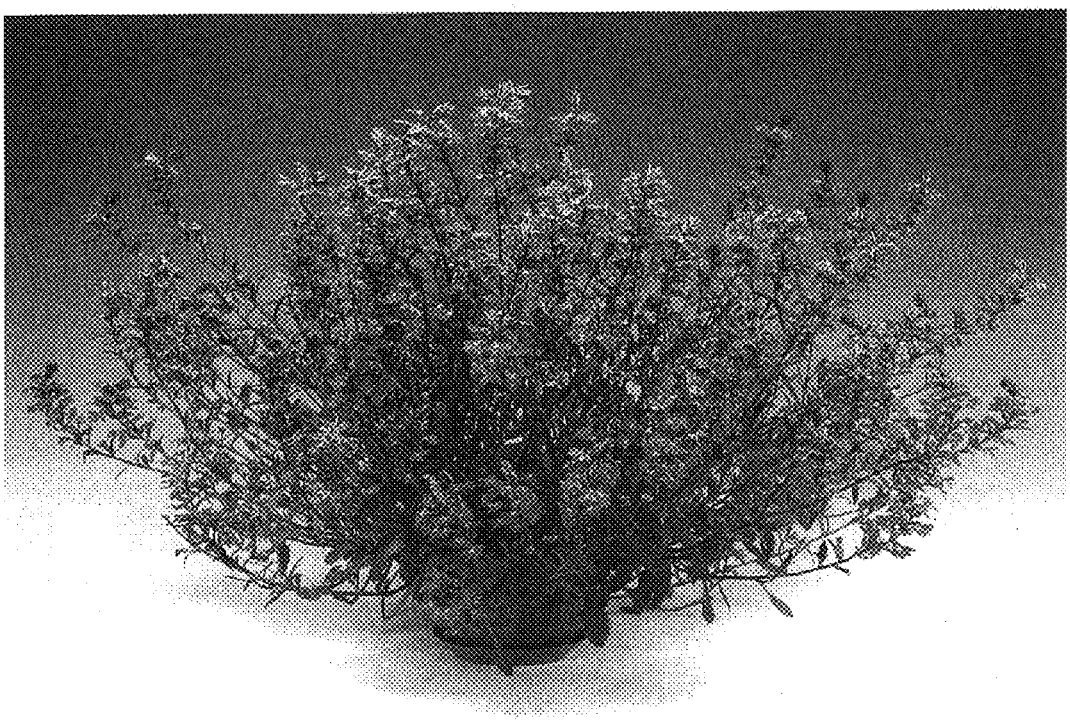

* * * * *